United States Patent
Borgschulte

(10) Patent No.: US 9,872,740 B2
(45) Date of Patent: Jan. 23, 2018

(54) ENDODONTIC SYSTEM AND METHOD

(71) Applicant: DENTSPLY International Inc., York, PA (US)

(72) Inventor: Markus Borgschulte, Munich (DE)

(73) Assignee: Dentsply Sirona Inc., York, PA (US)

( * ) Notice: Subject to any disclaimer, the term of this patent is extended or adjusted under 35 U.S.C. 154(b) by 160 days.

(21) Appl. No.: 14/195,120

(22) Filed: Mar. 3, 2014

(65) Prior Publication Data

US 2014/0315147 A1    Oct. 23, 2014

Related U.S. Application Data

(63) Continuation of application No. 13/267,272, filed on Oct. 6, 2011, now Pat. No. 8,714,978.

(30) Foreign Application Priority Data

Oct. 6, 2010  (EP) ..................... 10013364

(51) Int. Cl.
| | | |
|---|---|---|
| A61C 5/02 | (2006.01) | |
| A61C 1/00 | (2006.01) | |
| A61C 5/40 | (2017.01) | |
| A61C 5/42 | (2017.01) | |

(52) U.S. Cl.
CPC ............ *A61C 1/0007* (2013.01); *A61C 1/003* (2013.01); *A61C 5/40* (2017.02); *A61C 5/42* (2017.02)

(58) Field of Classification Search
CPC .. A61C 5/02; A61C 5/04; A61C 5/023; A61C 5/045; A61C 13/30
USPC ....................................... 433/224
See application file for complete search history.

(56) References Cited

U.S. PATENT DOCUMENTS

| | | | | |
|---|---|---|---|---|
| 3,578,745 | A * | 5/1971 | Garnier ................... | A61C 1/07 433/102 |
| 6,293,795 | B1 * | 9/2001 | Johnson ............... | A61C 1/0015 433/102 |
| 6,955,536 | B1 * | 10/2005 | Buchanan ............ | A61C 1/0015 433/27 |
| RE39,174 | E * | 7/2006 | Buchanan .............. | A61C 5/023 433/102 |
| 7,980,853 | B2 * | 7/2011 | Riitano ................... | A61C 5/023 433/224 |
| 8,714,978 | B2 * | 5/2014 | Borgschulte ........... | A61C 1/003 433/118 |
| 9,017,076 | B2 * | 4/2015 | Danger .................. | A61C 1/003 433/224 |
| 2003/0056561 | A1 * | 3/2003 | Butscher .................. | A61C 7/04 72/295 |
| 2012/0107766 | A1 * | 5/2012 | Borgschulte ........... | A61C 1/003 433/102 |

(Continued)

FOREIGN PATENT DOCUMENTS

WO    WO 2013076106 A2 *   5/2013   ............. F16H 19/08

*Primary Examiner* — Cris L Rodriguez
*Assistant Examiner* — Matthew Saunders
(74) *Attorney, Agent, or Firm* — David A. Zdurne; Douglas J. Hura; Leana Levin

(57) ABSTRACT

The present invention provides a system for the endodontic treatment of a root canal that includes (i) an endodontic instrument; (ii) an endodontic handpiece having a drive motor for rotating the endodontic instrument releasably attached to the handpiece; (iii) a control unit for controlling the rotation of the endodontic instrument according to one or more predetermined rotational sequences.

13 Claims, 3 Drawing Sheets

(56) References Cited

U.S. PATENT DOCUMENTS

2012/0122055 A1* 5/2012 Ramos ................... A61C 1/003
　　　　　　　　　　　　　　　　　　　　　　　433/102
2012/0225406 A1* 9/2012 Yared ............................ 433/102

* cited by examiner

ENDODONTIC SYSTEM AND METHOD

RELATED APPLICATIONS

This application is a Continuation of U.S. application Ser. No. 13/267,272 filed Oct. 6, 2011 and European patent application number EP 10013364.4 filed Oct. 6, 2010.

FIELD OF THE INVENTION

The present invention relates to a system for the endodontic treatment of a root canal. Furthermore, the present invention also relates to a method for operating the system for the endodontic treatment of a root canal.

BACKGROUND OF THE INVENTION

Effective cleaning and shaping of the root canal system is essential for achieving the biological and mechanical objectives of root canal treatment (Sjögren et al. 1997). The objectives are to remove all the pulp tissue, bacteria and their by-products while providing adequate canal shape to fill the canal.

Traditionally, the shaping of root canals was achieved by the use of stainless steel hand files. However, techniques using stainless steel hand files have several drawbacks:
1. They require the use of numerous hand files and drills to adequately prepare the canals (Schilder 1974).
2. Hand instrumentation with stainless steel files is time consuming (Ferrazetal. 2001).
3. The stainless steel hand instrumentation techniques have an increased incidence of canal transportation (Kuhn et al. 1997, Reddy & Hicks 1998, Ferraz et al. 2001, Pettiette et al. 2001).
4. Finally, from a clinical standpoint, the use of hand instruments in narrow canals can be very frustrating especially in teeth with difficult access.

Moreover, canal curvature has always introduced complexity into canal preparation. The "balanced force concept," i.e. small clockwise and counter clockwise movements, was developed over a period of 12 years, and proposed in 1985 by Roane as a means of overcoming the curvature influence. Using the balanced force technique, it is possible to shape curved canals with larger diameter hand instruments. The use of stainless steel hand instruments, however, is time-consuming and strenuous, and there is a high frequency of preparation errors.

The development of continuous rotary preparation with nickel-titanium instruments solved some of these issues, although it is still necessary to use several hand and rotary files in different steps, and there may be a lengthy learning curve before proficiency can be achieved. In fact, NiTi instruments offer many advantages over conventional stainless steel files. They are flexible (Walia et al. 1988), have increased cutting efficiency (Kazemi et al. 1996) and have improved time efficiency (Ferraz et al. 2001). Furthermore, NiTi instruments maintain the original canal shape during preparation and have a reduced tendency to transport the apical foramen (Kuhn et al. 1997, Reddy & Hicks 1998, Ferraz et al. 2001, Pettiette et al. 2001).

However, as these techniques also require the use of numerous instruments to enlarge the canal to an adequate size and taper, they are relatively time consuming.

Also, the use of hand instruments (for example to create a glide path prior to using a rotary instrument), which can be very frustrating in narrow canals in teeth with a limited access, is required. With continuous rotary NiTi systems it is necessary to create a glide path in order to minimize the risk of fracture. During the use of a rotary instrument, the tip of the instrument may bind in the canal. The motor will keep rotating the instrument while the tip of the instrument is bound. The instrument will rotate past its plastic limit and will eventually fracture at a specific angle of rotation. For this reason, it is necessary to create an initial glide path, or a minimal canal enlargement, before using continuous rotary instruments. The glide path will minimize the incidence of instrument binding and, therefore, minimize the risk of fracture.

The use of only one engine-driven instrument in reciprocation to prepare a root canal was published in the International Endodontic Journal (Yared 2008). The article described the use of an F2 ProTaper instrument. However, the use of that instrument in reciprocation presented two drawbacks:
1. Instrument fracture by cyclic fatigue in relation to the relative rigidity of the instrument due to its size, taper and cross-section.
2. The necessity of creating a glide path with additional hand files prior to using the F2 instrument in reciprocation.

SUMMARY OF THE INVENTION

It is the problem of the present invention to provide a system for the endodontic treatment of a root canal wherein only a single instrument is required to enlarge the canal and wherein hand files for enlarging the root canal prior to using the single file are not required, and whereby even a narrow and curved canal, may be prepared to an adequate size and taper.

Moreover, it is the problem of the present invention to provide a method for operating an endodontic system for the endodontic treatment of a root canal wherein only a single instrument is required to enlarge the canal and wherein hand files for enlarging the root canal prior to using the single file are not required, and whereby even a narrow and curved canal may be prepared to an adequate size and taper.

Accordingly, the present invention provides a system for the endodontic treatment of a root canal, comprising an endodontic instrument; an endodontic handpiece having a drive motor for rotating the endodontic instrument releasably attached to the handpiece; a control unit for controlling the rotation of the endodontic instrument according to one or more predetermined rotational sequences; the rotational sequences comprising reciprocating the endodontic instrument by continuously sequentially rotating the endodontic instrument in a first direction followed by reversing the direction of rotation so that $$0.5 \times \Psi \leq \alpha \leq \Psi \text{ and } 3 \leq \alpha/\beta \leq 20,$$

wherein $\alpha$ represents a rotational angle in a direction in which the rotating endodontic instrument removes debris from the root canal, $\beta$ represents a rotational angle in the opposite direction, and $\Psi$ represents the elastic angle of the endodontic instrument at which plastic deformation occurs in the direction of $\alpha$.

Moreover, the present invention relates to a method for operating the system for the endodontic treatment of a root canal, the method comprising reciprocating an endodontic instrument by continuously sequentially rotating the endodontic instrument in a first direction followed by reversing the direction of rotation so that $$0.5 \times \Psi \leq \alpha \leq \Psi \text{ and } 3 \leq \alpha/\beta \leq 20,$$

wherein α, β, and Ψ are as defined above. x in the formulae indicates the mathematical operation of multiplication and/ indicates the mathematical operation of division.

The present invention is based on the recognition that root canal preparation may be accomplished using only a single specific engine-driven instrument in reciprocation and without prior hand filing. This new concept goes against the current teaching standard, which requires the gradual enlargement of the canal with different files/instruments until the desired shape is obtained. In particular, the system and method of the present invention does not require the creation of a glide path with smaller instruments prior to using a shaping instrument to minimize the incidence of fracture. According to the present invention, the shaping instrument will follow the existing and natural path of least resistance, which is the root canal, which is not only time-saving but also particularly convenient in teeth with limited access. Additionally, errors associated with the use of hand filing prior to using mechanically driven instruments can be avoided.

DETAILED DESCRIPTION OF PREFERRED EMBODIMENTS

Figure 1:
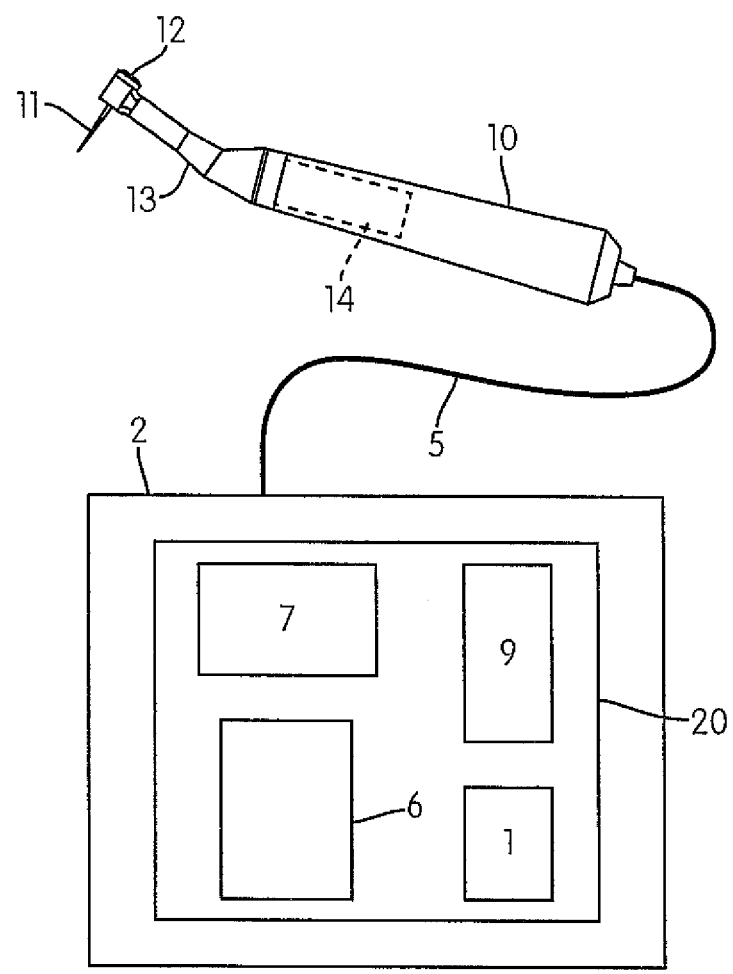
FIG. 1 is a schematic representation of a system for the endodontic treatment of a root canal according to the present invention.

FIG. 1 shows a system for the endodontic treatment of a root canal in accordance with one embodiment of the present invention. The system 2 comprises a handpiece 10 and a control unit 20.

An endodontic file 11 is releasably secured in a chuck of the handpiece head 12. The handpiece 10 further comprises a drive motor 14 fastened to a contra angle 13. The drive motor 14 is connected by a cable 5 to the control unit 20 which includes a microprocessor 9. The control unit 2 may further contain a memory 1, a keyboard 6 and a display 7. The control unit 20 controls the drive motor 4. Thereby, the control unit 20 controls the rotation of the endodontic instrument 11 according to one or more predetermined rotational sequences. In a cordless embodiment, the control unit 20 may be incorporated into the handpiece 10 and the system is battery operated. In a preferred embodiment, the drive motor is battery operated.

A memory 1 may be used to store predetermined rotational sequences for an endodontic treatment; as well as a library of operational parameters.

In accordance with the invention, the microprocessor 9 is configured to execute a predetermined rotational sequence. The predetermined rotational sequence comprises reciprocating the endodontic instrument by continuously sequentially rotating the endodontic instrument in a first direction followed by reversing the direction of rotation so that $$0.5 \times \Psi \leq \alpha \leq \Psi \text{ and } 3 \leq \alpha/\beta \leq 20,$$

wherein α represents a rotational angle in a direction in which the rotating endodontic instrument removes debris from the root canal, β represents a rotational angle in the opposite direction, and Ψ represents the elastic angle of the endodontic instrument at which plastic deformation occurs in the direction of α. In reciprocation, the endodontic instrument is driven first in a cutting direction and then reverses to release the instrument. According to the present invention, the angles of reciprocation are precise and specific to the design of the endodontic instrument and to the drive motor. One complete rotation of 360° is completed in several reciprocating movements.

According to an alternative embodiment, the control unit may be implemented as a mechanical means which does not require electric energy for controlling the rotational sequence.

Figure 3:
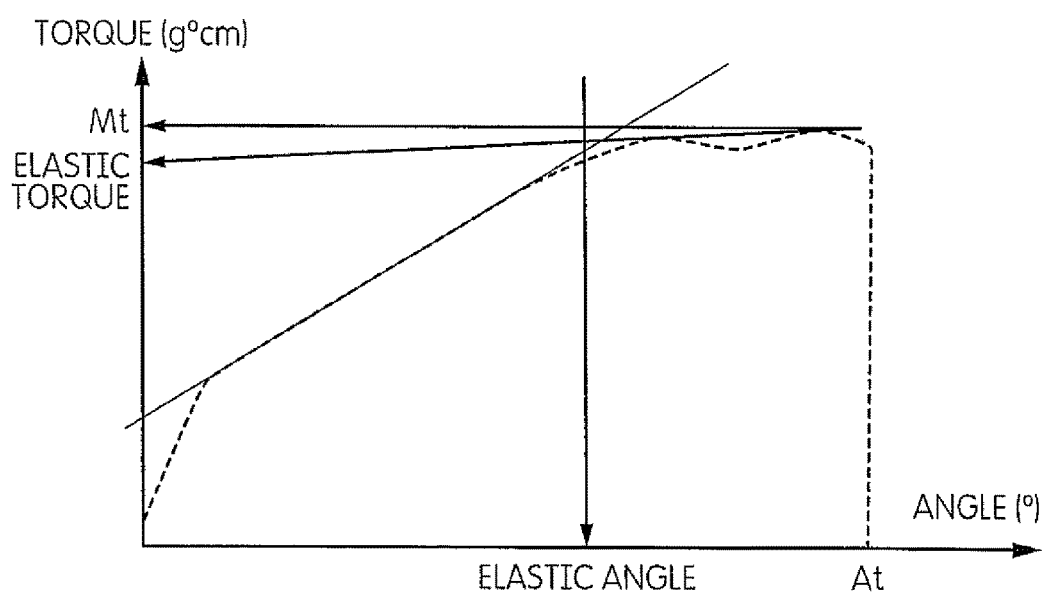
FIG. 3 shows an example of a diagram for determining the elastic angle Ψ of an endodontic instrument used according to the present invention.

According to a preferred embodiment, the reciprocating of the endodontic instrument is controlled so that 0.7× Ψ≤α<0.9×Ψ, and Ψ and α are as defined above. According to a further preferred embodiment, the reciprocating of the endodontic instrument is controlled so that 3.5≤α/β≤20, more preferably 4.0≤α/β≤10 and α and β are as defined above. The elastic angle Ψ of the endodontic instrument at which plastic deformation occurs in the direction of α is determined based on DIN EN ISO 3630-1:2008-04. Specifically, the test is carried out on an instrument to determine the elastic torque limit and the elastic angle, whereby the endodontic instrument is fixed at 3 mm from the tip and rotated at 2 rpm until fracture occurred. The function of the elastic torque over the rotational angle in the direction of α is recorded. The elastic angle value Ψ is calculated by the interpretation of the graph obtained during the torque resistance test as illustrated in FIG. 3. Specifically, the elastic angle is the intersection of the tangent of the region of elastic deformation and the tangent tangent of the region of plastic deformation of the endodontic instrument as represented in a torque diagram as shown in FIG. 3. The elastic angle value Ψ may be considered as the limiting rotational angle where any further rotation will result in a permanent plastic deformation of the endodontic instrument. The elastic angle value Ψ depends on the material and the shape of the endodontic instrument.

According to a further preferred embodiment the endodontic instrument has an elastic angle Ψ in the range of from 120 to 420°, more preferably 150 to 400° and still more preferably 190 to 390°. The preferred material for the endodontic instrument used according to the invention comprises a NiTi alloy.

According to a further preferred embodiment, the control unit further controls one or more parameters of the rotational sequence, said parameters being selected from the frequency of reciprocation ($F_r$), the number of reciprocation cycles ($N_r$) and the torque ($T_r$) exerted on the file.

According to the invention, the specific value of Ψ determines the limits of α and β. Accordingly, if, for example, Ψ is 240° for a given endodontic instrument, then α as the rotational angle in a direction in which the rotating endodontic instrument removes debris from the root canal is in the range of from 120° to less than 240°. Selecting α to be 180°, then β as the rotational angle in the opposite direction is in the range of from 9° to 60°. According to the invention, it is preferred to increase the difference between α and β in the rotational sequence so that the efficiency of the system is improved.

Furthermore, according to a preferred embodiment, the control unit of the system of the present invention may also use Ψ to determine $F_r$, $N_r$, and/or $T_r$.

Furthermore, the control unit may control the frequency of reciprocation (Fr) in a range of from 5 to 30 Hz, more preferably in a range of from 5 to 20 Hz.

Figures 2, 2A, 2B, 2C:
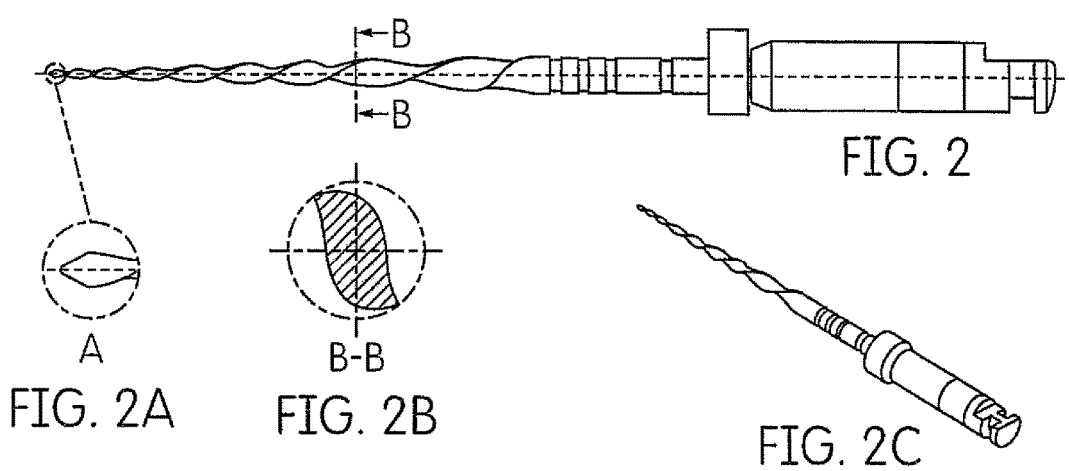
FIG. 2 shows an endodontic instrument used in the system of the present invention.

FIG. 2a shows an embodiment of a preferred endodontic instrument according to the present invention. Accordingly, the endodontic instrument has one or more spiral flutes or grooves. The endodontic instrument 100 includes a portion for securing the instrument to a handpiece, and an elongate shaft having cutting edges for shaping the tooth. A portion of the shaft comprises a working length having helical flutes which form the cutting edges of the endodontic instrument 100. In use, the working length of the instrument 100 is inserted into a root canal of a tooth through an upper interior portion of the tooth which has been initially opened using another instrument, such as a drill (not shown). The instrument 10 of the present invention is adapted for use with power operated equipment. The instrument 100 may be rotated in the direction of arrows A and/or reciprocated in the direction of arrow B to clean out and enlarge the root canal. Referring to FIG. 2b, a cross-sectional view of a portion of the working length of the instrument 10 is shown, wherein the helical configuration has been eliminated for clarity. In the exemplary embodiment shown, the instrument 10 has two cutting edges defined by two flutes 22 and two peripheral flute surfaces that extend from the cutting edges to trailing edges, in directions opposite the cutting direction The endodontic instrument may be an instrument having a diameter at the tip in the range of from 0.20 to 0.35 mm and a taper over the first 3 mm from the tip in the range of taper of from 7 to 9% and a diameter D16 in the range of from 1.00 to 1.10 mm; or an endodontic instrument having a diameter at the tip in the range of from 0.35 to 0.55 mm and a taper over the first 3 mm from the tip in the range of taper of from 5 to 7% and a diameter D16 in the range of from 1.05 to 1.15 mm; or an endodontic instrument having a diameter at the tip in the range of from 0.45 to 0.65 mm and a taper over the first 3 mm from the tip in the range of taper of from 4 to 6% and a diameter D16 in the range of from 1.12 to 1.22 mm.

In a further embodiment, the system of the present invention may be combined with additional dental devices, such as an apex locator, an endodontic instrument identification system, a vitality tester, a working length measurement system, a gutta-percha cutter, gutta-percha condenser, or a photo-polymerization lamp.

According to a preferred embodiment, the system according to the invention for single file reciprocation without prior use of hand files includes three instruments, (R25, R40 and R50), and a motor.

The R25 preferably has a diameter of 0.25 mm at the tip and an 8% (0.08 mm/mm) taper over the first 3 mm from the tip. The diameter at D16 is 1.05 mm.

The R40 has a diameter of 0.40 mm at the tip and a 6% (0.06 mm/mm) taper over the first 3 mm from the tip. The diameter at D16 is 1.10 mm.

The R50 has a diameter of 0.50 mm at the tip and a 5% (0.05 mm/mm) taper over the first 3 mm from the tip. The diameter at D16 is 1.17 mm.

Only one instrument is used for the canal preparation depending on the initial size of the canal. Preferably, the instruments are made from an M-Wire nickel-titanium that offers greater flexibility and resistance to cyclic fatigue than traditional nickel-titanium. Preferably, the instruments have an S-shaped cross-section and a regressive taper.

Preferably, the motor is battery operated. The battery may be rechargeable and the motor can be used while the battery is charging. The instruments are preferably used at about 5 to 30, or typically at about 10 cycles of reciprocation per second. 10 cycles represent the equivalent of approximately 300 rpm. The motor is preferably programmed with the angles of reciprocation and speed for the three instruments.

When the instrument rotates in the cutting direction it will advance in the canal and engage dentine to cut it. When it rotates in the opposite direction (smaller rotation) the instrument will be immediately disengaged. The end result is an advancement of the instrument in the canal. Consequently, only very light apical pressure on the instrument is required, as its advancement is almost automatic. The angles are specific to the endodontic instruments and are determined using the torsional properties of the instruments namely the elastic angle $\Psi$ of the endodontic instrument at which plastic deformation occurs in the direction of $\alpha$.

The method for operating the system for the endodontic treatment of a root canal according to the present invention, comprises reciprocating the endodontic instrument by continuously sequentially rotating the endodontic instrument in a first direction followed by reversing the direction of rotation so that $0.5 \times \Psi \leq \alpha < \Psi$ and $3 \leq \alpha/\beta \leq 20$. According to a preferred embodiment, the method may further comprise (i) rotating the endodontic instrument in a first rotational direction to remove material when a control parameter is below a first threshold value, (ii) reciprocating the endodontic instrument when the control parameter is greater than or equal to the first threshold value, and (iii) rotating the endodontic instrument only in the rotational direction opposite to the first rotational direction in order to free the instrument, when the control parameter is greater than or equal to a second threshold value that is greater than the first threshold value.

According to a preferred embodiment, the control parameter is the torque applied to the endodontic instrument.

The method for preparing a root canal with a single file will now be illustrated by the following example. Accordingly, only one endodontic instrument is usually used in reciprocation to complete the canal preparation and there is no need for hand filing. The access cavity requirements, the straight-line access to the canals and the irrigation protocol are the same as for standard preparation techniques. It is not necessary to widen the root canal orifice with a Gates Glidden drill or an orifice opener.

Selection of the Appropriate Endodontic Instrument:

Selection of the appropriate endodontic instrument is based on an adequate preoperative radiograph. If the canal is partially or completely invisible on the radiograph, the canal is considered narrow and, for example, the R25 is selected. In the other cases, where the radiograph shows the canal clearly from the access cavity to the apex, the canal is considered medium or wide. A size 30 hand instrument may be inserted passively (with a gentle watch winding movement but without filing action) to the working length. If it reaches the working length, the canal is considered large and the R50 may be selected for the canal preparation. If the size 30 hand file does not passively reach working length, a size 20 hand file is inserted passively to the working length. If it reaches working length, the canal is considered medium and the R40 may then be selected for the canal preparation. If the size 20 hand instrument does not reach the working length passively, the R25 may be selected.

Preparation Step by Step (without Creating a Glide Path):

In reciprocation, clockwise and counter clockwise angles determine the amplitude of reciprocation, the right and left rotations. These angles are lower than the angles at which the endodontic instrument would usually fracture (if bound). When a reciprocating file binds in the canal, it will not rotate past its specific angle of fracture. Therefore, the creation of a glide path to minimize binding is not required for the endodontic instruments. The cutting efficiency of the endodontic instruments and the centering ability associated with reciprocation allow the instruments to enlarge uninstrumented and narrow canals in a safe manner.

Before commencing preparation, the length of the root canal is estimated with the help of an adequately exposed and angulated pre-operative radiograph. A silicone stopper may be set on the instrument at ⅔ of that length. The endodontic instrument is introduced in the canal with a slow in-and-out pecking motion without pulling the instrument completely out of the canal. The amplitude of the in- and out-movements should preferably not exceed 3-4 mm. Only very light pressure should preferably be applied. The instrument will advance easily in the canal in an apical direction. After three in- and out-movements, or when more pressure is needed to make the instrument advance further in the canal, or when resistance is encountered, the instrument may be pulled out of the canal to clean the flutes. A #10 file may be used to check patency to ⅔ of the estimated working length. The canal may preferably be copiously irrigated.

The endodontic instrument is preferably used until it has reached ⅔ of the estimated working length as indicated by the stopper on the instrument. The instrument may then be removed from the canal, the canal may preferably be irrigated and a #10 file may be used to determine the length. The endodontic instrument may then be re-used in the same manner until the working length has been reached. As soon as the working length has been reached, the endodontic instrument is withdrawn from the canal. The endodontic instrument can also be used in a brushing motion against the lateral walls of wide canals. The endodontic instrument will be used to working length to complete the preparation.

The invention claimed is:

1. A system for the endodontic treatment of a root canal, comprising
   (i) an endodontic instrument;
   (ii) an endodontic handpiece having a drive motor for rotating the endodontic instrument releasably attached to the handpiece;
   (iii) a control unit for controlling the rotation of the endodontic instrument according to one or more predetermined rotational sequences; the rotational sequences comprising reciprocating the endodontic instrument by continuously sequentially rotating the endodontic instrument in a first direction followed by reversing the direction of rotation so that $0.5 \times \psi \leq \alpha < \psi$ and $3 \leq \alpha/\beta \leq 20$,
   wherein $\alpha$ represents a rotational angle in a direction in which the rotating endodontic instrument removes debris from the root canal, $\beta$ represents a rotational angle in the opposite direction, and $\psi$ represents the elastic angle of the endodontic instrument at which plastic deformation occurs in the direction of $\alpha$; and
   wherein the control unit controls a frequency of reciprocation ($F_r$) in a range of from 5 to 30 Hz.

2. The system for the endodontic treatment of a root canal according to claim 1, wherein $0.7 \times \psi \leq \alpha < 0.9 \times \psi$, and $\alpha$ and $\psi$ are as defined in claim 1.

3. The system for the endodontic treatment of a root canal according to claim 1, $4 \leq \alpha/\beta \leq 10$, and $\alpha$ and $\beta$ are as defined in claim 1.

4. The system for the endodontic treatment of a root canal according to claim 1, wherein the control unit further controls one or more parameters of the rotational sequence, said parameters being selected from the frequency of reciprocation ($F_r$), the number of reciprocation cycles ($N_r$) and the torque ($T_r$) exerted on the file.

5. The system for the endodontic treatment of a root canal according to claim 1, wherein $\alpha$, $\beta$, $F_r$, $N_r$, and/or $T_r$ are predetermined based on $\psi$.

6. The system for the endodontic treatment of a root canal according to claim 1, wherein the endodontic instrument has an elastic angle ($\psi$) in the range of from 120 to 420°.

7. The system for the endodontic treatment of a root canal according to claim 1, wherein the endodontic instrument comprises a NiTi alloy.

8. The system for the endodontic treatment of a root canal according to claim 1, wherein the endodontic instrument has a non-cutting tip.

9. The system for the endodontic treatment of a root canal according to claim 1, wherein the endodontic instrument has one or more spiral grooves.

10. The system for the endodontic treatment of a root canal according to claim 1, wherein the endodontic instrument has a diameter at the tip in the range of from 0.20 to 0.35 mm and a taper over the first 3 mm from the tip in the range of taper of from 7 to 9% and a diameter D16 in the range of from 1.00 to 1.10 mm; or wherein the endodontic instrument has a diameter at the tip in the range of from 0.35 to 0.55 mm and a taper over the first 3 mm from the tip in the range of taper of from 5 to 7% and a diameter D16 in the range of from 1.05 to 1.15 mm; or wherein the endodontic instrument has a diameter at the tip in the range of from 0.45 to 0.65 mm and a taper over the first 3 mm from the tip in the range of taper of from 4 to 6% and a diameter D16 in the range of from 1.12 to 1.22 mm.

11. The system for the endodontic treatment of a root canal according to claim 1, wherein the drive motor is battery operated.

12. A method for operating the system for the endodontic treatment of a root canal, the method comprising the steps of: reciprocating an endodontic instrument in a first rotational direction when a control parameter is less than or equal to a threshold value, wherein the control parameter is a number of reciprocation cycles; and further when the control parameter is greater than the threshold value reciprocating the endodontic instrument by continuously sequentially rotating the endodontic instrument in the first direction followed by a rotational direction opposite of the first rotational direction so that $0.5 \times \psi \leq \alpha \leq \psi$ and $3 \leq \alpha/\beta \leq 20$, wherein $\alpha$ represents a rotational angle in a direction in which the rotating endodontic instrument removes debris from the root canal, $\beta$ represents a rotational angle in the opposite direction, and $\psi$ represents the elastic angle of the endodontic instrument at which plastic deformation occurs in the direction of $\alpha$.

13. The method for operating the system for the endodontic treatment of a root canal according to claim 12, wherein method further comprises reciprocating the endodontic instrument when the control parameter is greater than or equal to the first threshold value, and rotating the endodontic instrument only in the rotational direction opposite to the first rotational direction in order to free the instrument, when the control parameter is greater than or equal to a second threshold value that is greater than the first threshold value.

* * * * *